US010806457B1

(12) United States Patent
Vanderpool et al.

(10) Patent No.: US 10,806,457 B1
(45) Date of Patent: Oct. 20, 2020

(54) INTRALUMINAL ANASTOMOTIC DEVICE AND METHOD

(71) Applicants: Charles H Vanderpool, Central Point, OR (US); Shaylene Tarvyd MacDonald, Torrance, CA (US); Scott Tarvyd MacDonald, Torrance, CA (US)

(72) Inventors: Charles H Vanderpool, Central Point, OR (US); Shaylene Tarvyd MacDonald, Torrance, CA (US); Scott Tarvyd MacDonald, Torrance, CA (US)

( * ) Notice: Subject to any disclaimer, the term of this patent is extended or adjusted under 35 U.S.C. 154(b) by 74 days.

(21) Appl. No.: 15/952,772

(22) Filed: Apr. 13, 2018

Related U.S. Application Data

(60) Provisional application No. 62/484,967, filed on Apr. 13, 2017.

(51) Int. Cl.

| | | |
|---|---|---|
| *A61B 17/295* | (2006.01) | |
| *A61B 17/11* | (2006.01) | |
| *A61B 6/00* | (2006.01) | |
| *A61B 34/20* | (2016.01) | |
| *A61B 17/22* | (2006.01) | |

(Continued)

(52) U.S. Cl.
CPC ........ *A61B 17/1114* (2013.01); *A61B 6/4057* (2013.01); *A61B 6/425* (2013.01); *A61B 17/295* (2013.01); *A61B 34/20* (2016.02); *A61B 2017/1117* (2013.01); *A61B 2017/1121* (2013.01); *A61B 2017/1125* (2013.01); *A61B 2017/1132* (2013.01); *A61B 2017/22071* (2013.01); *A61B 2017/306* (2013.01); *A61B 2017/32004* (2013.01); *A61B 2017/320024* (2013.01); *A61N 2005/1021* (2013.01)

(58) Field of Classification Search
CPC ......... A61B 17/1114; A61B 2017/1117; A61B 2017/1121; A61B 2017/306; A61B 2017/1125; A61B 17/42; A61B 17/4241; A61B 17/320016; A61B 17/32002
See application file for complete search history.

(56) References Cited

U.S. PATENT DOCUMENTS

| | | | |
|---|---|---|---|
| 5,839,639 A | * | 11/1998 | Sauer ................... A61B 17/115 227/175.1 |
| 6,083,241 A | | 7/2000 | Longo et al. |

(Continued)

FOREIGN PATENT DOCUMENTS

| | | |
|---|---|---|
| WO | WO1991002491 | 3/1991 |

*Primary Examiner* — George J Ulsh
*Assistant Examiner* — Andrew P. Restaino
(74) *Attorney, Agent, or Firm* — Eric Karich; Karich & Associates (57) ABSTRACT

A surgical tool has an elongate tubular housing having an annular clamping region formed around an opening in the tubular housing. A vacuum source is operably engaged with the elongate tubular housing for providing a vacuum within the elongate tubular housing for drawing the damaged or diseased portion of a luminal body, such as an intestine, into the tubular housing. An elongate rod is provided having an annular clamping element shaped so that the intestine may be firmly clamped between the annular clamping element and the annular clamping region of the elongate tubular housing, so that the damaged or diseased portion of the intestine is entirely within the elongate tubular housing.

8 Claims, 8 Drawing Sheets

(51) Int. Cl.
*A61B 17/32* (2006.01)
*A61B 17/30* (2006.01)
*A61N 5/10* (2006.01)

(56) References Cited

U.S. PATENT DOCUMENTS

| | | | |
|---|---|---|---|
| 6,117,148 A * | 9/2000 | Ravo | A61B 17/115 227/180.1 |
| 7,141,055 B2 | 11/2006 | Abrams et al. | |
| 7,210,609 B2 | 5/2007 | Leiboff et al. | |
| 8,361,090 B2 | 1/2013 | Belson | |
| 2003/0158563 A1* | 8/2003 | McClellan | A61B 17/12009 606/151 |
| 2012/0010633 A1* | 1/2012 | Noda | A61B 17/12013 606/140 |

* cited by examiner

INTRALUMINAL ANASTOMOTIC DEVICE AND METHOD

CROSS-REFERENCE TO RELATED APPLICATIONS

This application for a utility patent claims the benefit of U.S. Provisional Application No. 62/484,967, filed Apr. 13, 2017.

BACKGROUND OF THE INVENTION

Field of the Invention

This invention relates generally to surgical devices, and more particularly to a intraluminal anastomotic device for performing luminal surgery.

Description of Related Art

The techniques of resecting a segment of a luminal structure, such as an intestine, and an anastomosis of the cut ends are common procedures where a segment of diseased bowel must be removed for reasons such as inflammation, oncological process, obstructions, bleeding, perforation, trauma, etc. A conventional procedure for resection and anastomosis is conducted laparoscopically or through opening the peritoneal cavity. Often in removing the interior segment, the lumen of the bowel is opened, exposing the contaminated area to the clean peritoneal cavity, increasing the risk of postoperative complications. Following the resection of the segment to be removed, the remaining ends of the bowel are anastomosed to guarantee the continuity of the intestinal track.

The prior art teaches anastomotic devices that are adapted for performing intraluminal intestinal reconstruction and resection through the anus with portions of the surgery being performed laparoscopically.

Ravo et al., U.S. Pat. No. 6,117,148, teaches an intraluminal intestinal reconstruction and resection anastomotic device that includes a cylindrical housing that is inserted into the bowel through the anus. The cylindrical housing includes an annular housing at the end, which includes a cutting mechanism, and a staple mechanism. Importantly, the Ravo device includes a central post (14) which extends from the housing along the centerline of the housing. The central post includes an annular groove which may be moved longitudinally along the central post. This annular groove is attached to the bowel with a ligation member (suture, flexible band, etc.), which is attached laparoscopically.

The present invention uses vacuum to draw the bowel into the cylindrical housing, thereby removing the need for a laparoscopic surgical ligation of the tool to the bowel. Since no laparoscopic surgery is required, the danger of infection and other complications is reduced.

SUMMARY OF THE INVENTION

The present invention teaches certain benefits in construction and use which give rise to the objectives described below.

The present invention provides a surgical tool for resection of a damaged or diseased portion of a luminal body such as an intestine or vascular, and anastomosis of the ends formed by the resection. The surgical tool includes a tubular housing having an opening. A vacuum source is operably engaged with the elongate tubular housing for providing a vacuum within the elongate tubular housing for drawing the damaged or diseased portion of the intestine into the tubular housing.

In one embodiment, the invention further includes an annular clamping region formed around the opening in the tubular housing, and an elongate rod having an annular clamping element shaped so that the intestine may be firmly clamped between the annular clamping element and the annular clamping region of the elongate tubular housing, so that the damaged or diseased portion of the intestine is entirely within the elongate tubular housing.

A primary objective of the present invention is to provide a surgical tool having advantages not taught by the prior art.

Another objective is to provide a surgical tool that enables a faster surgical procedure, with a less invasive surgical method, which enables the use of less anesthetic and faster recovery time.

A further objective is to provide a surgical tool that reduces the danger of sepsis by limiting and containing any cuts to the intestines, and avoiding or minimizing any invasion of the abdominal cavity.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, an intraluminal anastomotic device in the form of a surgical tool for resection of a damaged or diseased portion of a luminal body, such as an intestine, vascular structure, or other similar structure, and anastomosis of the ends formed by the resection. The surgical tool enables a surgical method that is performed entirely from within the luminal body, without requiring any accompanying laparoscopic procedures that intrude into the abdominal cavity.

Figure 1:
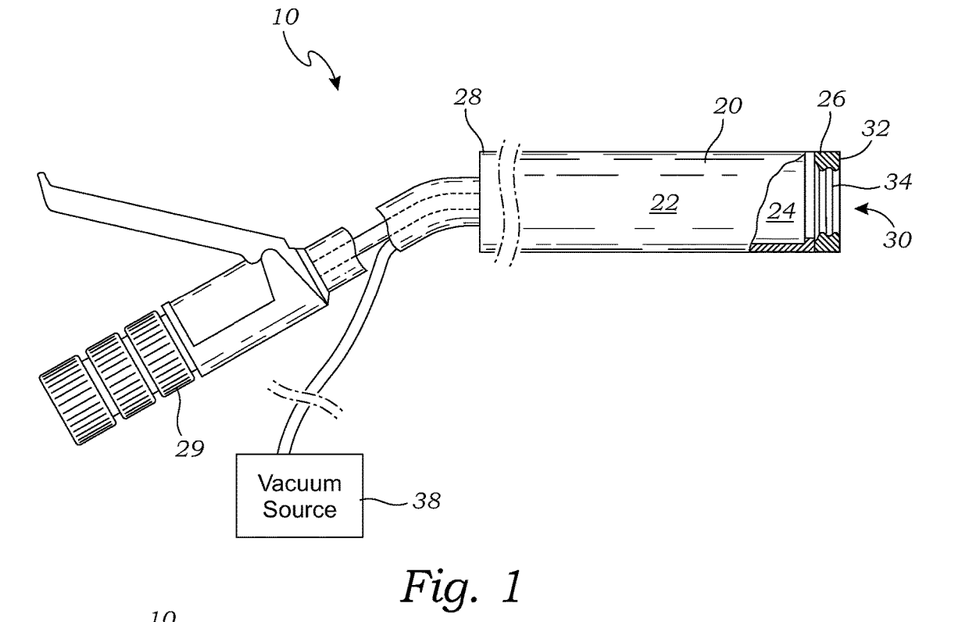
FIG. 1 is a perspective view of a intraluminal anastomotic device according to one embodiment of the present invention.

FIG. 1 is a perspective view of one embodiment of the surgical tool 10. As shown in FIG. 1, the surgical tool 10 includes an elongate tubular housing 20 having an outer surface 22 and an inner surface 24 that extend from a proximal end 26 to a distal end 28. The proximal end 26 is adapted to be inserted into the luminal body, in this case into the intestine 12 via the anus of the patient, as discussed in greater detail below. The distal end 28 receives a control mechanism 29 which enable the doctor to operate the surgical tool 10, as discussed in greater detail below.

In the embodiment of FIG. 1, the surgical tool 10 includes an annular clamping region 32 formed around an opening 30 in the tubular housing 20. In this embodiment, the opening 30 may be formed at the proximal end 26, and the annular clamping region 32 may be formed on the inner surface 24 adjacent the proximal end 26 of the tubular housing 20. As discussed in greater detail below, the opening 30 and the annular clamping region 32 may alternatively be formed in other locations (e.g., the sidewall of the surgical tool 10, as shown in FIGS. 8-11). In this embodiment, the annular clamping region 32 forms an annular depression 34, which is adapted for gripping the intestine 12, as discussed in greater detail below.

The operation of the surgical tool 10 is controlled via the control mechanism 29, shown in FIG. 1, and the sequential operation of the surgical tool 10 is schematically illustrated in FIGS. 2-6. Since the control mechanism 29 structure and function is known in the prior art, it is not discussed in greater detail herein.

Figure 3:
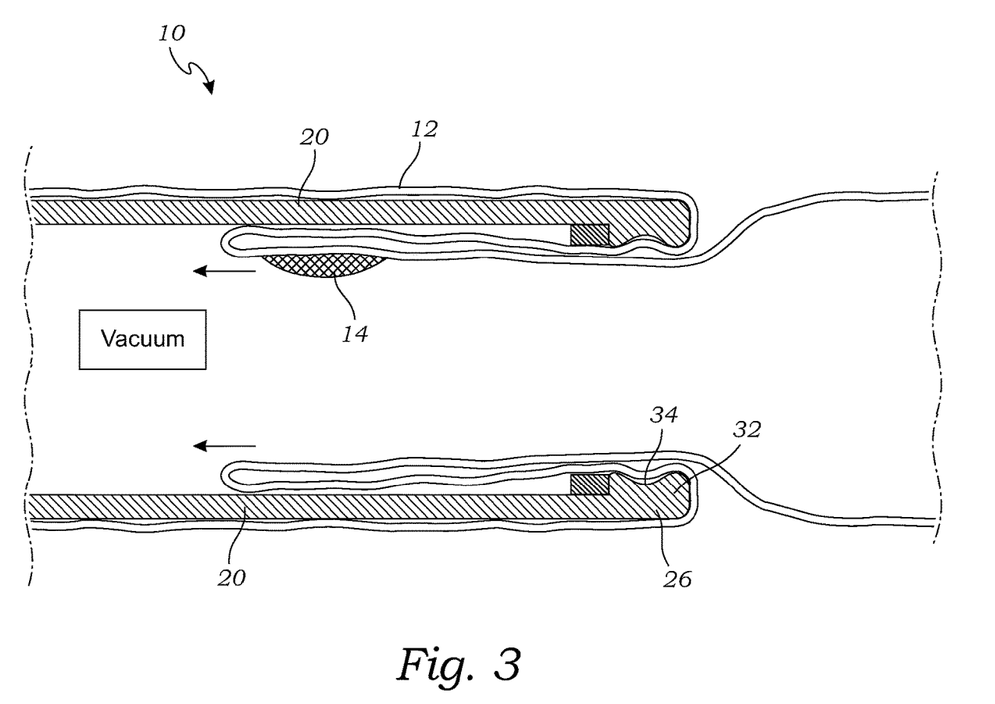
FIG. 3 is a cross sectional schematic view of the anastomotic device during intussusception of a damaged or diseased portion of the intestine.

The surgical tool 10 further includes a vacuum source 38 operably engaged with the elongate tubular housing 20 for providing a vacuum within the elongate tubular housing 20 for drawing the damaged or diseased portion of the intestine 12 into the tubular housing 20, as shown in FIG. 3, and as discussed in greater detail below. The vacuum source 38 may be any form of vacuum pump, cannister, or other mechanism or source known in the art.

Figure 2:
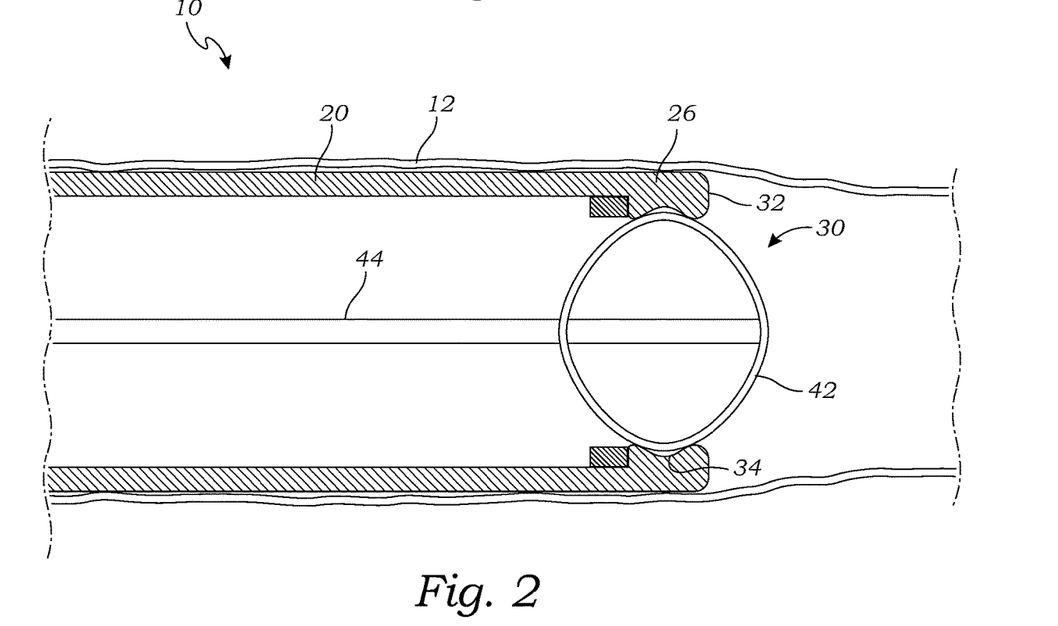
FIG. 2 is a cross sectional schematic view of the anastomotic device being inserted into a patient's intestine.

FIG. 2 is a cross sectional schematic view of the surgical tool 10 being inserted into a patient's intestine 12. As shown in FIG. 2, the tubular housing 20 of the surgical tool 10 is introduced into the intestine 12 through the anus. In this embodiment, a guide balloon 42 is operatively positioned to facilitate insertion. The guide balloon 42 may be mounted on an elongate rod 44, which is operatively controlled via the control mechanism 29 shown in FIG. 1. Following insertion, this is deflated and removed. The elongate rod 44 may be extended up an axis of the tubular housing 20 to the annular clamping element 46 (or other suitable location).

FIG. 3 is a cross sectional schematic view of the surgical tool 10 during intussusception of a damaged or diseased portion of the intestine 12. As shown in FIG. 3, at a predetermined location below the damaged or diseased section 14 of the intestine 12 to be removed, the vacuum source 38 (shown in FIG. 1) is used to create a vacuum within the tubular housing 20. When this vacuum is induced, the damaged or diseased section 14 of the intestine 12 is pulled into the tube. When the desired amount of the intestine 12 is within the tubular housing 20, the vacuum is released, and the intestine 12 may be secured in place and discussed below.

Figure 4:
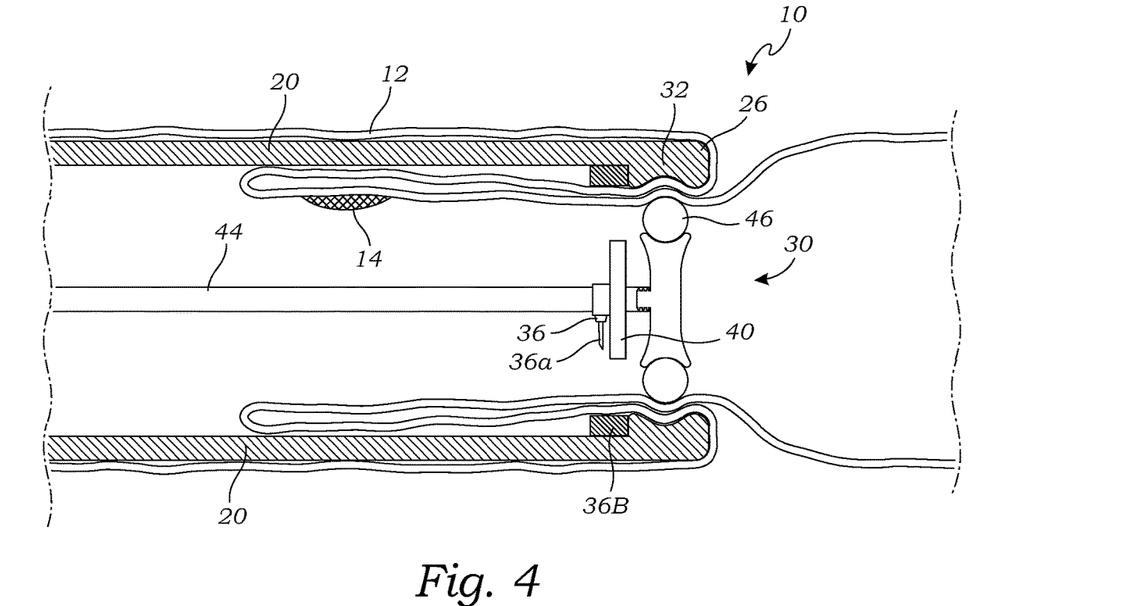
FIG. 4 is a cross sectional schematic view of the anastomotic device being used to clamp sections of the intestine on either side of the damaged or diseased section of the intestine.

FIG. 4 is a cross sectional schematic view of the surgical tool 10 being used to clamp the intestine 12 on either side of the damaged or diseased portion of the intestine 12. As shown in FIG. 4, a clamp is used to clamp/pinch both layers of the intestine 12 against the inside wall of the tube. This clamp immobilizes the intestine 12 and pinches off any blood flow. In the present embodiment, the intestine 12 may be firmly clamped between the annular clamping element 46 and the annular clamping region 32, so that the damaged or diseased portion of the intestine 12 is entirely within the elongate tubular housing 20. In this embodiment, the annular clamping element 46 is a ring of flexible material that may be inflated or otherwise expanded to clamp the intestine 12, as shown. The annular clamping element 46 may be mounted on the end of the elongate rod 44, or other suitable structure.

Figure 5:
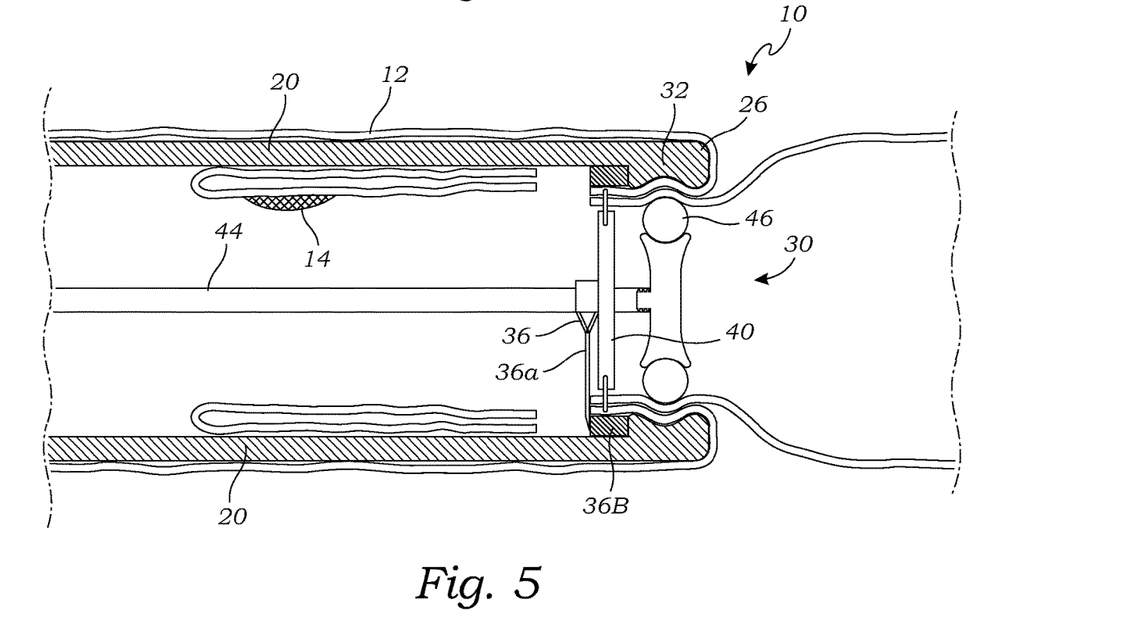
FIG. 5 is a cross sectional schematic view of the anastomotic device being used to cut the intestine on either side of the damaged or diseased section of the intestine, forming cut ends, and to staple or suture the cut ends of the intestine together.

FIG. 5 is a cross sectional schematic view of the surgical tool 10 being used to cut the intestine 12 on either side of the damaged or diseased portion of the intestine 12, forming cut ends 16, and to staple or suture the cut ends 16 of the intestine 12 together. As shown in FIGS. 4 and 5, in this embodiment, once the intestine 12 has been clamped/pinched, it is simultaneously cut and stapled/sutured. Due to the cutting system, cutting both layers at the same time, they exactly align. This pinching and holding is of a huge advantage to surgeons. The ends of the intestine 12, still attached to the body, are then sutured together and the clamp is released.

In this embodiment, beneath the annular clamping region 32, a cutting mechanism 36 is provided which includes a cutting blade 36A (e.g., knife) and an annular hardened cutting ring 36B against which the knife can cut. The cutting mechanism 36 is adapted for cutting the intestine 12 adjacent the annular clamping region 32, forming cut ends 16 of the intestine 12. The surgical tool 10 further includes an anastomosis mechanism 40 for attaching the cut ends 16 together. The anastomosis mechanism 40 may include an including mechanical connections such as staples, compression rings, biological connectors such as glue, or other connection mechanisms known in the art for this purpose. Since similar anastomosis mechanisms 40 are known in the art, this mechanism is not described in greater detail herein, and the disclosure of Ravo et al., U.S. Pat. No. 6,117,148, is incorporated herein by reference in its entirety.

Figure 6:
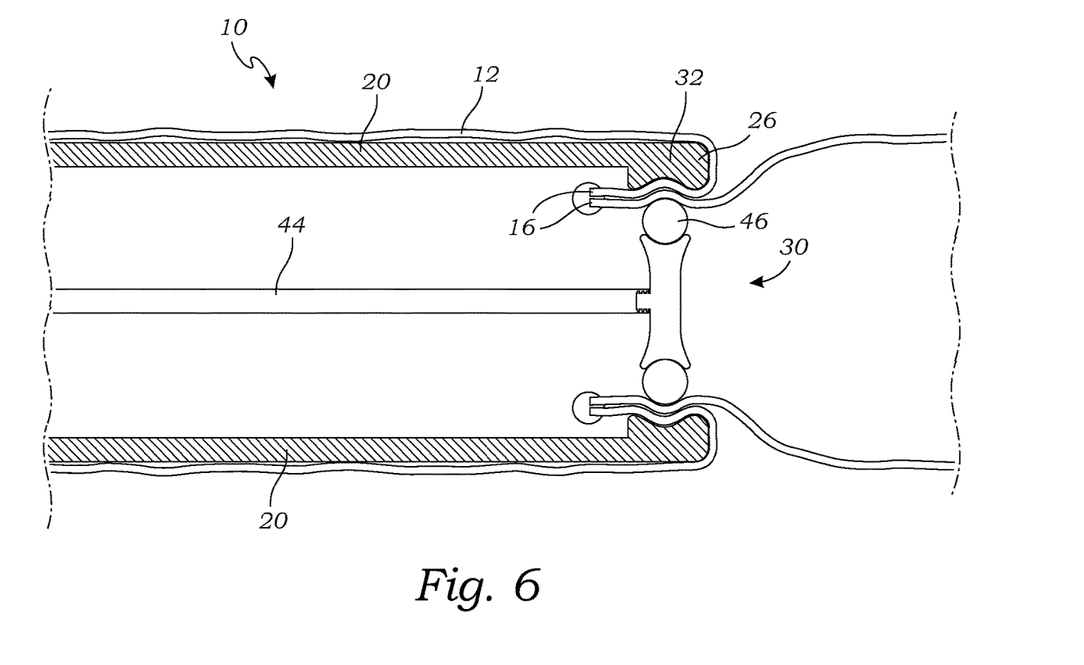
FIG. 6 is a cross sectional schematic view of the surgical tool once the cutting and stapling process has been complete.

FIG. 6 is a cross sectional schematic view of the surgical tool 10 once the cutting and stapling process has been complete. As shown in FIG. 6, the intestine 12 may remain clamped throughout the entire cutting/stapling process, thereby minimizing any danger of contamination.

Figure 7:
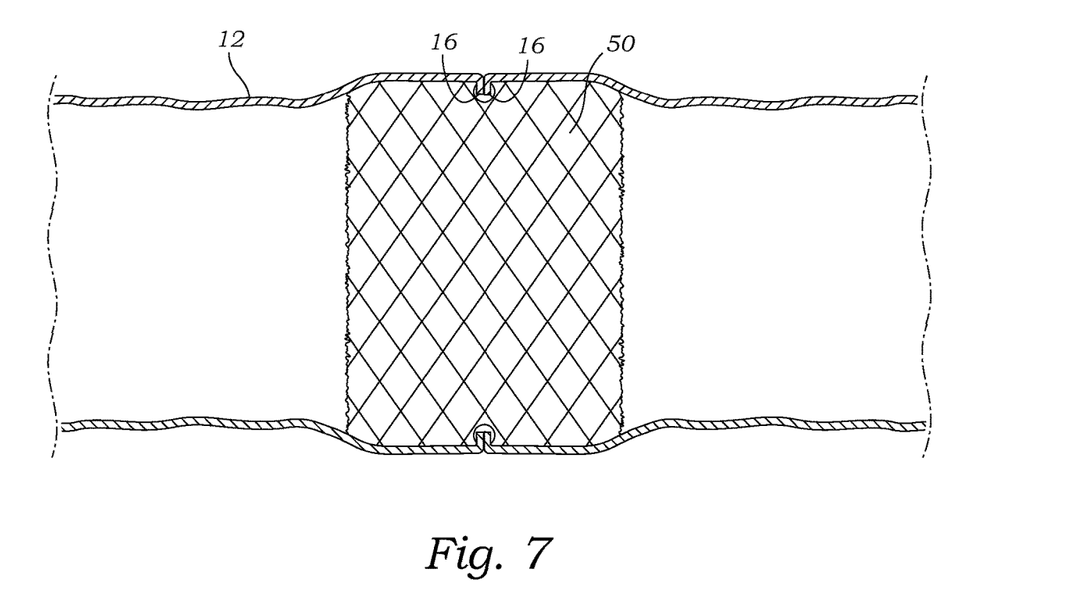
FIG. 7 is a cross sectional schematic view of the intestine once a stent has been positioned to overlap the stapled or sutured portion of the intestine.

FIG. 7 is a cross sectional schematic view of the intestine 12 once a stent 18 has been positioned overlapping the stapled or sutured portion of the intestine 12. The stent 18, which may be dissolvable, may be left behind to keep the intestine 12 from constricting.

Figure 8:
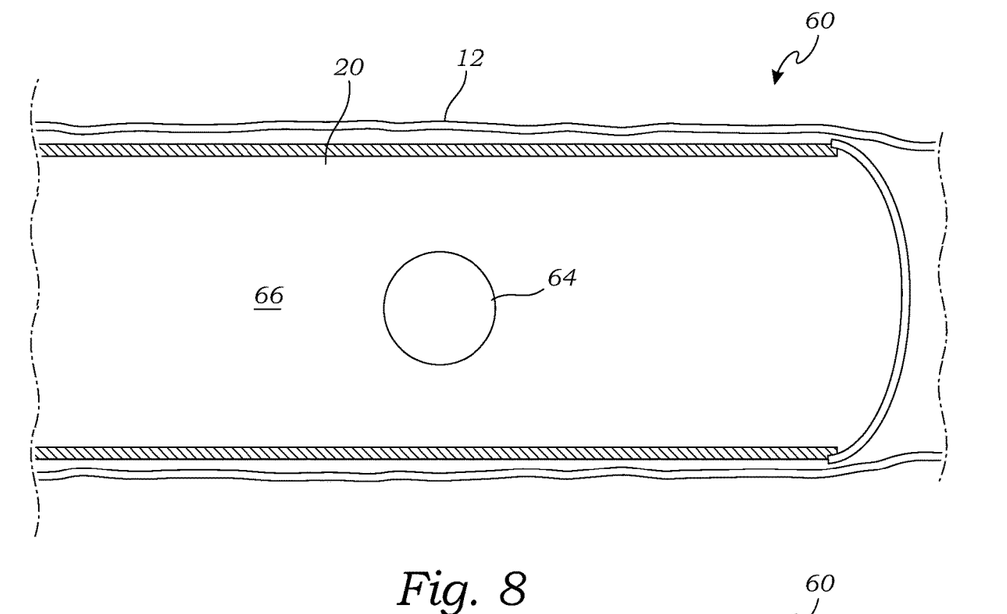
FIGS. 8-11 are cross sectional schematic views illustrating the structure and function of a second embodiment of the anastomotic device being used to remove a diverticula'
Figure 9:
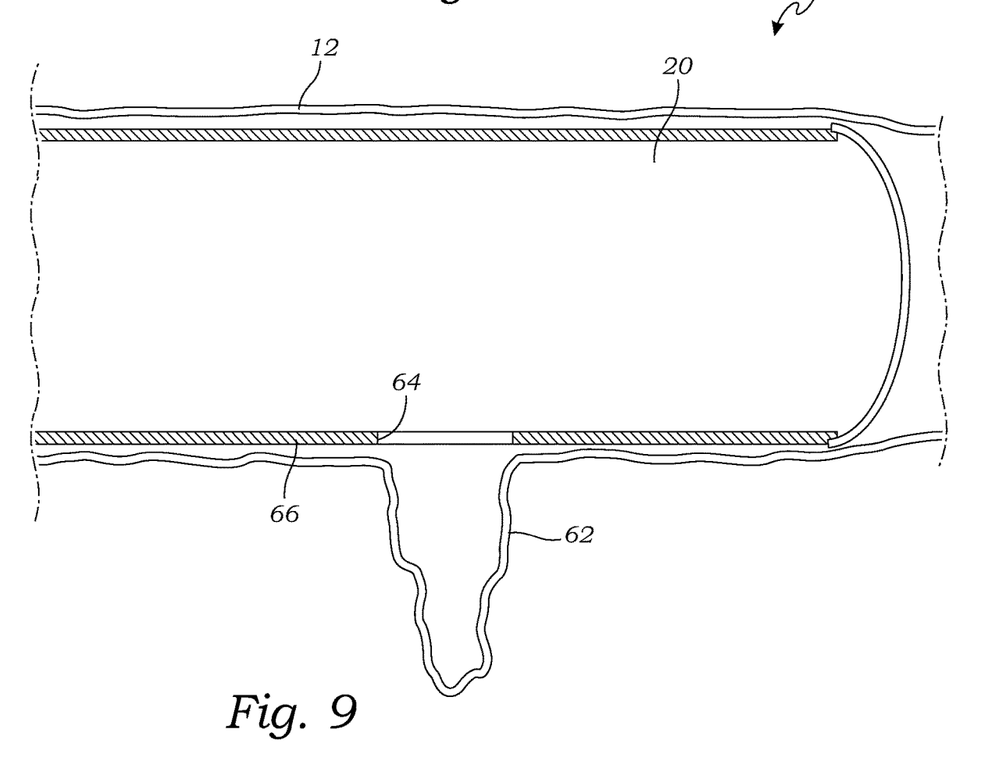
Figure 10:
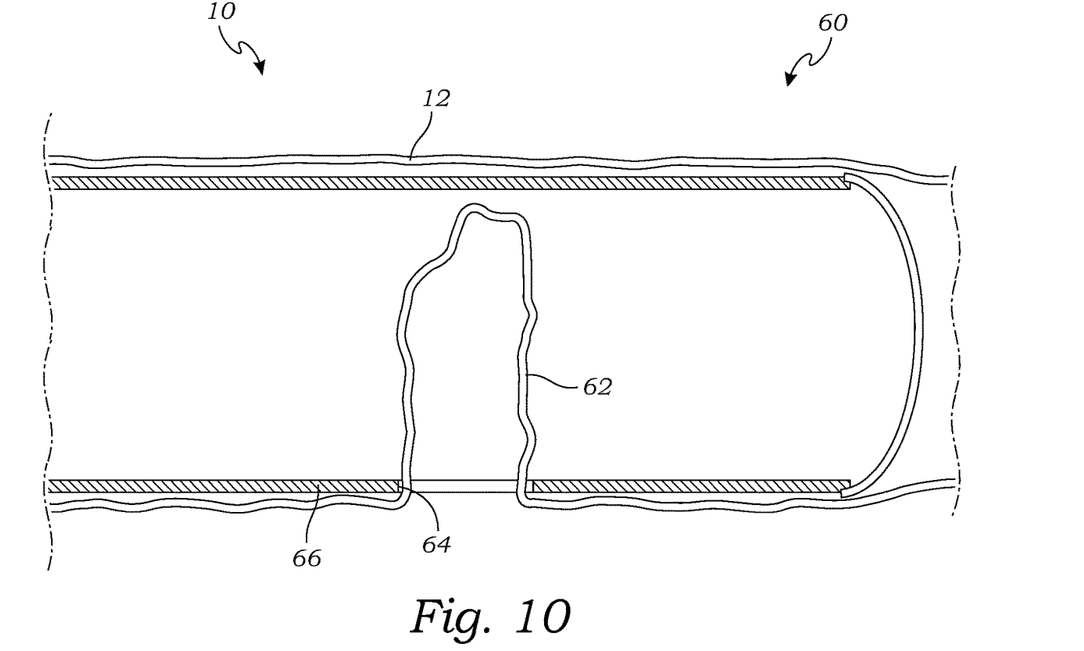
Figure 11:
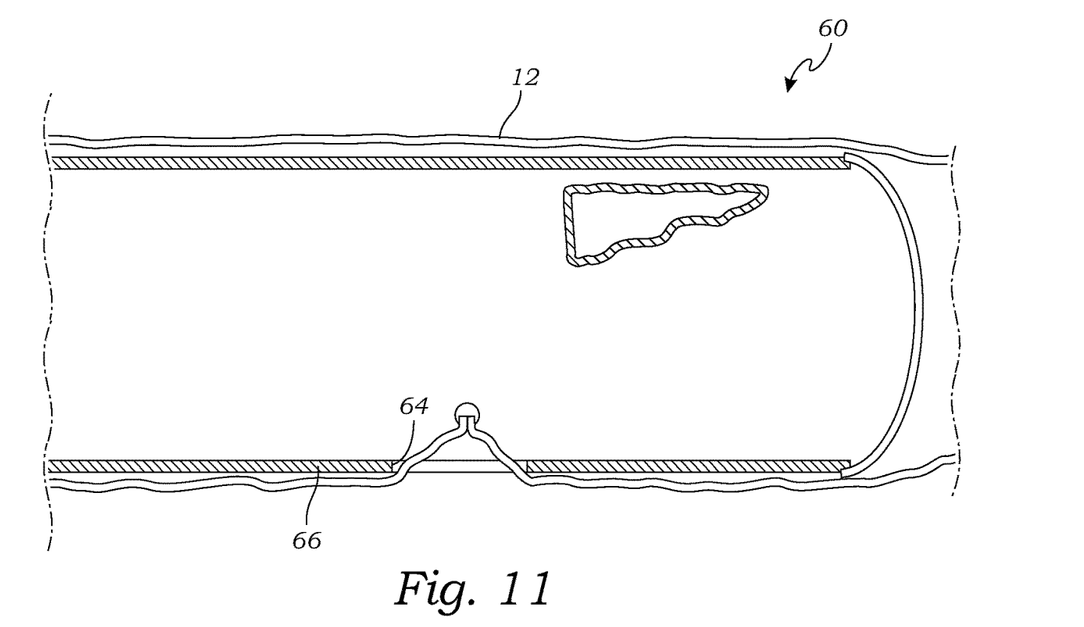

FIGS. 8-11 are cross sectional schematic views illustrating the structure and function of a second embodiment of the surgical tool 60 being used to remove a diverticula 62. As shown in FIGS. 8-11, the tubular housing 20 may also be used to invert a diverticula 62 prolapse. In this embodiment, the proximal end 26 of the tubular housing 20 is closed, and the opening 64 is provided in the side 66 of the tube, as shown in FIG. 8. After the tubular housing 20 has been inserted into the intestine 12, the opening 30 is aligned with the prolapse, as shown in FIG. 9. Once vacuum has been applied, as shown in FIG. 10, the prolapse will invert. If the prolapse has adhesions on the outside, these must be cut away using a laparoscopic procedure. The cutting and stitching of the intestine 12 may be performed using currently available surgical instruments.

Figure 12:
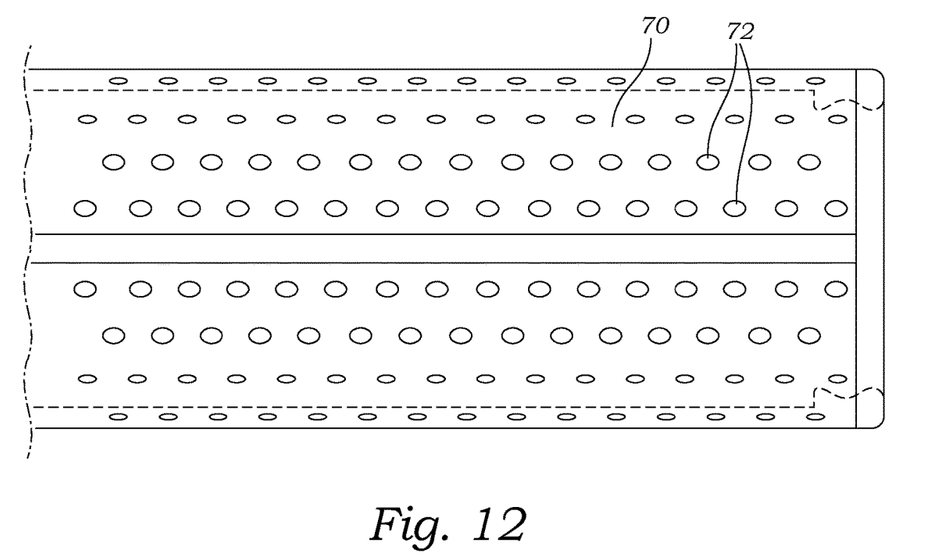
FIG. 12 is a side view of sliding panels of the anastomotic device.

FIG. 12 is a side view of sliding panels 70 of the surgical tool which may be provided in some embodiments of the invention. The panels 70 are movably (i.e., slidably) mounted on the tubular housing 20, and include a plurality of holes 72 which may be operably attached to the vacuum source 38 (shown in FIG. 1) and/or a source of gas pressure (not shown). When vacuum is applied, the suction causes the panels 70 to adhere to the inside of the intestine 12, thereby allowing the panels 70 to pull the head into the intestine 12 or push out of the intestine 12. To release the intestine 12, the vacuum may be released, or the panel 70 may use gas pressure to push the intestine 12 away from the panel 70 allowing movement of that panel 70 relative to the intestine 12.

Figure 13:
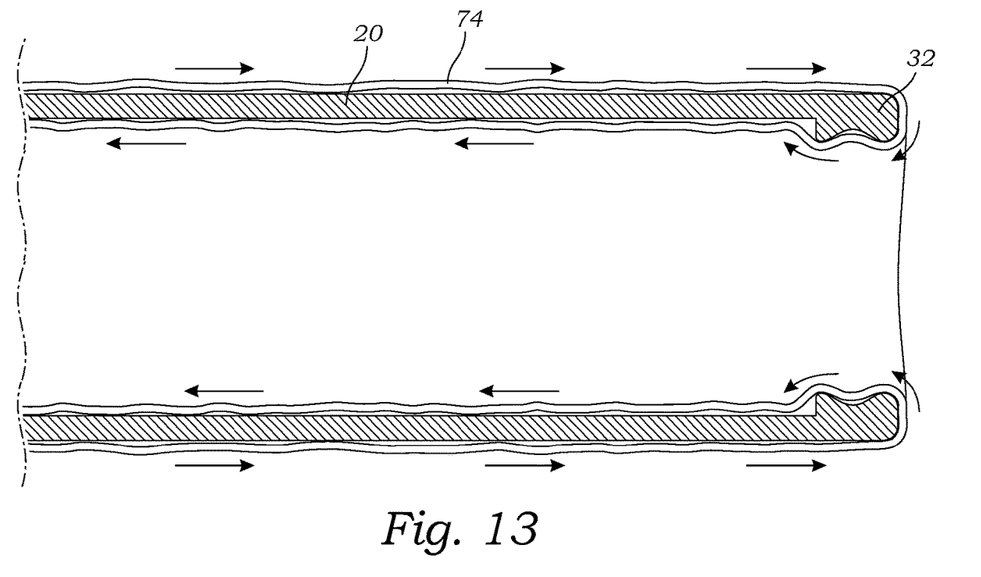
FIG. 13 is a cross sectional schematic view of a plastic sheath being used to insert the anastomotic device.

FIG. 13 is a cross sectional schematic view of a plastic sheath 74 being used to insert the surgical tool 10. The plastic sheath 74 covers both inside and out of the tubular housing 20, including the annular clamping region 32. This plastic sheath 74 can be pulled into the suction head, thereby reducing the chance of any cancer metastasizing from transfer through contact (smearing) with the annular clamping region 32. When the choice is made to use this plastic sheath 74, the annular clamping region 32 could be placed as close as possible to the site to be removed. Once there when suction is induced the plastic sheath 74 is induced to move from the outside to the inside of the annular clamping region 32. If the plastic is moved in at the same rate as the intestine 12 is drawn in, cancerous tissue never touches the device. When using this plastic sheath 74, the plastic sheath 74 would move when compared to the annular clamping region 32 yet stay still in comparison to the cancer site. The cancer and the plastic sheath 74 would be pulled into the suction head at the same rate. To accomplish this, the annular clamping region 32 would be pulled toward the anus, at the same time as the intestine 12 was being pulled into the annular clamping region 32. This would result in approximately equal amounts of intestine 12 to be removed from each side of the cancer site.

Figure 14:
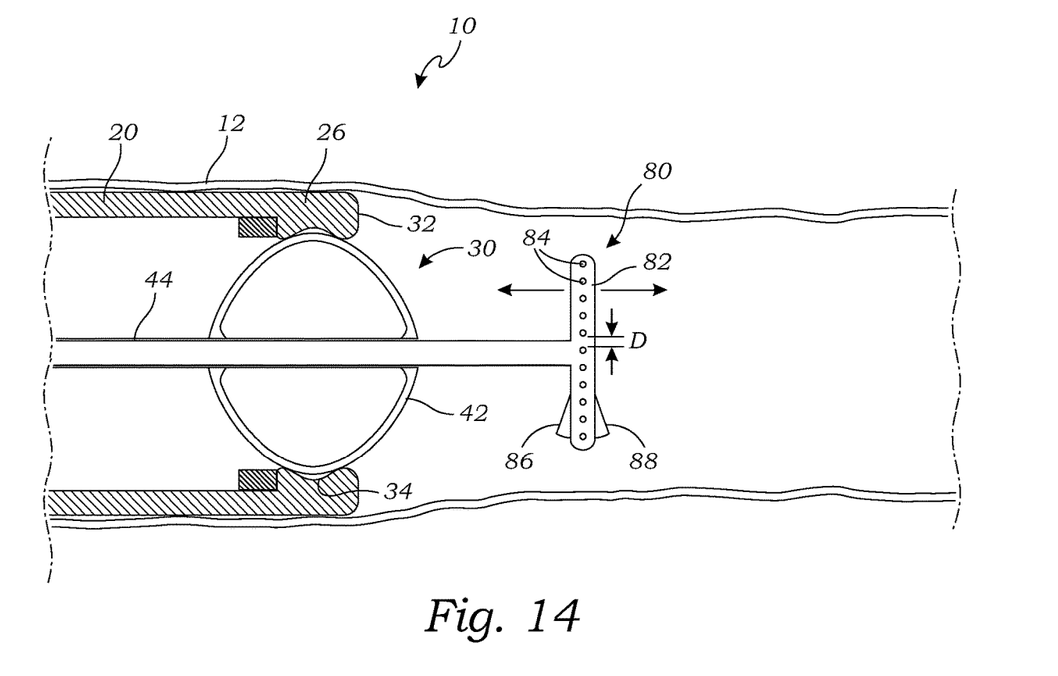
FIG. 14 is a cross sectional schematic view of the anastomotic device being guided through a patient's intestine with an ionizing radiation detector.

FIG. 14 is a cross sectional schematic view of the surgical device 10 being guided through a patient's intestine with a radiation detector device 80. The direction of movement of the radiation detector device 80 is longitudinally, as shown, is along the axis of the intestine, in front of the guide balloon 42. The radiation detector device 80 includes, in this embodiment, an annular housing 82 that includes a plurality of vacuum holes 84 around the perimeter of the radiation detector device 80. The holes 84 may be spaced a distance D from one another. The radiation detector device 80 may include an marking device 86 (e.g, inkjet printing mechanism, or other marking mechanism known in the art). It also includes a radiation detector 88 for detecting radiation. The radiation detector device 80 is advanced to the desired location, at which time the vacuum holes 84 are used to lock onto the intestine, using vacuum from the vacuum source 38 of FIG. 1 (or another suitable source), thereby controlling the length of cut by the inward or outward motion of the length of cut probe.

The radiation detector 88 allows the surgeon to detect radioactive isotopes used to both degrade cancers and mark their location. The marking device 86 allow surgeons to mark where they will do intestinal removal. The radiation detector device 80 is mounted on the support shaft 44 which also carries the controls for the operation of the device 80.

As used in this application, the words "a," "an," and "one" are defined to include one or more of the referenced item unless specifically stated otherwise. The terms "approximately" and "about" are defined to mean+/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is not limited to these embodiments, but rather the scope of the invention is defined by the following claims.

What is claimed is:

1. A surgical tool for resection of a damaged or diseased portion of an intestine, and anastomosis of cut ends of the intestine formed by the resection, the surgical tool comprising:
   an elongate tubular housing having an outer surface and an inner surface that extend from a proximal end to a distal end, an opening being formed at the proximal end;
   a vacuum source operably engaged with the elongate tubular housing for providing a vacuum within the proximal end of the elongate tubular housing, adjacent the opening, for drawing the damaged or diseased portion of the intestine into the elongate tubular housing;
   an annular clamping region formed on the inner surface of the elongate tubular housing adjacent the proximal end of the tubular housing, and around the opening;
   an annular cutting ring positioned on the inner surface of the elongate tubular housing adjacent the annular clamping region, opposite the opening;
   an elongate rod that extends up an axis of the tubular housing;
   an annular clamping element mounted on the elongate rod so that the intestine may be firmly clamped between the annular clamping element and the annular clamping region on the inner surface of the elongate tubular housing adjacent the proximal end of the tubular housing, so that the damaged or diseased portion of the intestine is entirely within the elongate tubular housing;
   an anastomosis mechanism for attaching the cut ends together, the anastomosis mechanism being mounted on the elongate rod adjacent the annular clamping element;
   a cutting mechanism mounted on the elongate rod adjacent the anastomosis mechanism, opposite the annular clamping element, for cutting outwardly through the intestine against the annular cutting ring.

2. The surgical tool of claim 1, wherein the opening is coaxial to the axis of the elongate tubular housing.

3. The surgical tool of claim 2, further comprising a guide balloon mountable upon the elongate rod for facilitating insertion of the surgical tool into the intestine of the patient.

4. The surgical tool of claim 3, wherein the guide balloon is mountable against the annular clamping region on the inner surface of the elongate tubular housing.

5. A method for resection of a damaged or diseased portion of an intestine of a patient, and anastomosis of cut ends of the intestine formed by the resection, via an anus of the patient, without any cutting into an abdominal cavity of the patient, the method comprising the steps of:

providing a surgical tool comprising:

an elongate tubular housing having an outer surface and an inner surface that extend from a proximal end to a distal end, an opening being formed at the proximal end;

an annular clamping region formed on the inner surface of the elongate tubular housing adjacent the proximal end of the tubular housing, and around the opening;

an annular cutting ring positioned on the inner surface of the elongate tubular housing adjacent the annular clamping region, opposite the opening;

an elongate rod that extends up an axis of the tubular housing;

an annular clamping element mounted on the elongate rod;

an anastomosis mechanism for attaching the cut ends together, the anastomosis mechanism being mounted on the elongate rod adjacent the annular clamping element; and         a cutting mechanism mounted on the elongate rod adjacent the anastomosis mechanism, opposite the annular clamping element, for cutting outwardly through the intestine against the annular cutting ring;

inserting the proximal end of the surgical tool into the intestine of the patient, via the anus, until the proximal end of the tubular housing is adjacent the damaged or diseased portion of the intestine;

providing a vacuum within the proximal end of the elongate tubular housing, adjacent the opening, thereby drawing the damaged or diseased portion of the intestine into the elongate tubular housing;

positioning the annular clamping element, via the elongate rod, within the intestine and seated against the annular clamping region, so that the intestine is firmly clamped between the annular clamping element and the annular clamping region on the inner surface of the elongate tubular housing, so that the damaged or diseased portion of the intestine is entirely within the elongate tubular housing;

forming an anastomosis of the intestine adjacent via the anastomosis mechanism adjacent the annular clamping element; and     cutting, from inside the intestine outwardly, the intestines adjacent the anastomosis using the cutting mechanism mounted on the elongate rod.

6. The method of claim 5, wherein the opening is coaxial to the axis of the elongate tubular housing.

7. The method of claim 6, further comprising a guide balloon mountable upon the elongate rod for facilitating insertion of the surgical tool into the intestine of the patient.

8. The method of claim 7, wherein the guide balloon is mountable against the annular clamping region on the inner surface of the elongate tubular housing.

\* \* \* \* \*